(12) United States Patent
Blecha et al.

(10) Patent No.: US 6,713,605 B1
(45) Date of Patent: Mar. 30, 2004

(54) SYNTHETIC PEPTIDES THAT INHIBIT LEUKOCYTE SUPEROXIDE ANION PRODUCTION AND/OR ATTRACT LEUKOCYTES

(75) Inventors: Frank Blecha, Manhattan, KS (US); Jishu Shi, Los Angeles, CA (US)

(73) Assignee: Kansas State University Research Foundation, Manhattan, KS (US)

(*) Notice: Subject to any disclaimer, the term of this patent is extended or adjusted under 35 U.S.C. 154(b) by 0 days.

(21) Appl. No.: 08/930,777

(22) PCT Filed: Apr. 10, 1996

(86) PCT No.: PCT/US96/04674

§ 371 (c)(1),
(2), (4) Date: Oct. 8, 1997

(87) PCT Pub. No.: WO96/32129

PCT Pub. Date: Oct. 17, 1996

(51) Int. Cl.[7] .................................. C07K 14/00
(52) U.S. Cl. .................... 530/324; 530/300; 514/12
(58) Field of Search ................ 530/324, 300; 514/12, 2

(56) References Cited

U.S. PATENT DOCUMENTS 5,726,155 A * 3/1998 Bokoch ................. 514/13

OTHER PUBLICATIONS

Sumimoto, Proc. Natl. Acad. Sci 91, 5345, 1994.*
Leto, Proc. Natl. Acad. Sci. 91, 10650, 1994.*

* cited by examiner

Primary Examiner—Christopher S. F. Low
Assistant Examiner—David Lukton
(74) Attorney, Agent, or Firm—Hovey Williams LLP

(57) ABSTRACT

Methods of inhibiting leukocyte $O_2^-$ production and attracting luekocytes using specific peptides are disclosed. Theses peptides include the proline-arginine (PR)-rich antimicrobial peptide known as PR-39 and truncated analogs thereof. These peptides can be used as medicaments that fight infection by attracting leukocytes to a wound site, yet restrict tissue damage at the wound site caused by excessive oxygen radicals produced by these leukocytes.

8 Claims, 12 Drawing Sheets

(−25 μM−)

SYNTHETIC PEPTIDES THAT INHIBIT LEUKOCYTE SUPEROXIDE ANION PRODUCTION AND/OR ATTRACT LEUKOCYTES

FEDERALLY SPONSORED RESEARCH OR DEVELOPMENT

This invention was made with government support under Grant No. 93-37206-9351 awarded by the USDA. The government has certain rights in the invention.

BACKGROUND OF THE INVENTION

1. Field of the Invention

The present invention is broadly concerned with methods of inhibiting leukocyte superoxide anion ($O_2^-$) production and methods of attracting a leukocyte to a location using peptides. More particularly, the invention relates to methods employing a naturally occurring proline-arginine (PR)-rich antimicrobial peptide known as PR-39 and analogs thereof; these peptides can be used as medicaments that fight infection by attracting leukocytes to a wound site, yet restrict tissue damage at the wound site caused by excessive oxygen radicals produced by these leukocytes.

2. Description of the Prior Art

Infectious diseases are a primary cause of morbidity and mortality in humans and animals. These maladies range from the troublesome, e.g., *Escherichia coli* diarrhea which is caused by the consumption of contaminated food and drinks, to the deadly, e.g., AIDS.

A variety of antimicrobial agents have been developed to combat infectious diseases. Recently, several types of antimicrobial peptides have been discovered. Such peptide antimicrobials are produced by many biological organisms and are important components of host defense mechanisms. (Boman, 1991; Zasloff, 1992; Gabay, 1994; Boman, 1995, Martin et al., 1995) For example, defensins are expressed in several mammalian species (Lehrer et al., 1993), magainins have been identified in the skin and intestine of frogs (Zasloff, 1987; Moore et al., 1992), and cecropins have been isolated from insects and pigs (Steiner et al., 1981; Lee et al., 1989). These natural antimicrobials are lytic peptides that kill microorganisms by pore-forming, membrane-damaging mechanisms (Boman et al., 1993; Maloy et al., 1995).

The patent art also discloses antimicrobial peptides. U.S. Pat. No. 5,234,716 describes broad spectrum tryptophan antimicrobial peptides, and U.S. Pat. No. 5,202,420 discloses tracheal antimicrobial peptides.

Recently, a group of PR-rich antibacterial peptides have been identified. Bactenecins 5 and 7 have been isolated from bovine neutrophils (Gennaro et al., 1989; Litteri et al., 1993), and PR-39 was first isolated from the porcine small intestine (Agerberth et al., 1991) and identified recently in porcine and human neutrophils (Shi et al., 1994b; Shi et al., 1995). Although these PR-rich antibacterial peptides share a similar high content of proline (47, 47, and 49%, respectively) and arginine (21, 29, and 26%, respectively), they possess different killing mechanisms.

Similar to other lytic peptides, bactenecins kill bacteria by a membrane-permeability-associated mechanism (Maloy et al., 1995); however, PR-39 was found to kill bacteria by interfering with DNA and/or protein synthesis (Boman et al., 1993). Furthermore, PR-39 has been isolated from wound fluid and was shown to induce syndecan expression on mesenchymal cells (Gallo, 1994). Because syndecans are important in wound repair, this finding suggests that PR-39, in addition to its antibacterial properties, may have a larger role in inflammatory processes and tissue repair.

Neutrophils represent a first line of defense against infections; they are the first white blood cells to arrive at sites of infection and are well-equipped to sequester and eliminate pathogens. These cells possess multiple antimicrobial defense mechanisms, including both oxidative and nonoxidative microbial killing processes (Klebanoff, 1992; Selsted et al., 1995). Nonoxidative neutrophil defense mechanisms include several antibacterial peptides including PR-39. Phagocyte oxidative defense mechanisms are initiated by a plasma membrane-bound enzyme complex called reduced nicotinamide dinucleotide phosphate (NADPH) oxidase (Rotrosen, 1992). This multicomponent enzyme catalyzes the reduction of molecular oxygen to $O_2^-$ using NADPH as an electron donor. Although $O_2^-$ and other reactive oxygen intermediates are important components of host defense, these highly toxic oxidants also cause significant tissue injury in inflammatory diseases and ischemia-reperfusion injury (Shasby et al., 1982: Malech, 1987; Demling, 1990; Martinez-Cayuela, 1995; Granger et al., 1995). Thus, their generation and inactivation must be tightly regulated.

At least five proteins comprise the NADPH oxidase complex; a membrane flavocytochrome $b_{558}$, which is composed of two subunits ($gp91^{phox}$ and $p22^{phox}$); and three cytosolic components ($p47^{phox}$, $p67^{phox}$, and a GTP-binding protein named $p21^{Rac}$) (Rotrosen et al., 1992; Abo et al., 1992). Although mechanisms for activation and assembly of NADPH oxidase have not been elucidated fully, it is clear that multiple protein-protein interactions among its components are regulated by a number of signaling intermediates (McPhail et al., 1993). The assembly of phagocyte NADPH oxidase requires protein-protein interactions between Src homology 3 (SH3) domains in cytosolic components and proline-rich regions in other components (Leto et al., 1994; Sumimoto et al., 1994; Finan et al. McPhail, 1994; de Mendez, 1996).

SUMMARY OF THE INVENTION

The present invention is predicated upon the discovery that specific peptides (e.g., PR-39) are capable of 1) inhibiting $O_2^-$ synthesis by leukocyte enzymes (e.g., NADPH oxidase), and 2) attracting leukocytes (e.g., neutrophils). These peptides can be used as novel medicaments that fight infection by attracting leukocytes to a wound site, yet restrict tissue damage at the wound site caused by excessive oxygen radicals produced by these leukocytes. Preferably, these peptides have a sequence included in PR-39 (e.g., Sequence ID Nos. 1 and 2 for peptides capable of inhibiting $O_2^-$ production, and Sequences ID Nos. 1, 2, 5, 6, and 7 for peptides capable of attracting leukocytes). Advantageously, these peptides are synthesized and have lengths of less than 60 amino acid residues, and the leucocytes upon which the peptides act are mammalian (e.g., porcine) leucocytes. This invention was made with government support under Grant 93-37206-9351 awarded by the United States Department of Agriculture. The government has certain rights in the invention.

DETAILED DESCRIPTION OF THE PREFERRED EMBODIMENT

Figure 1:
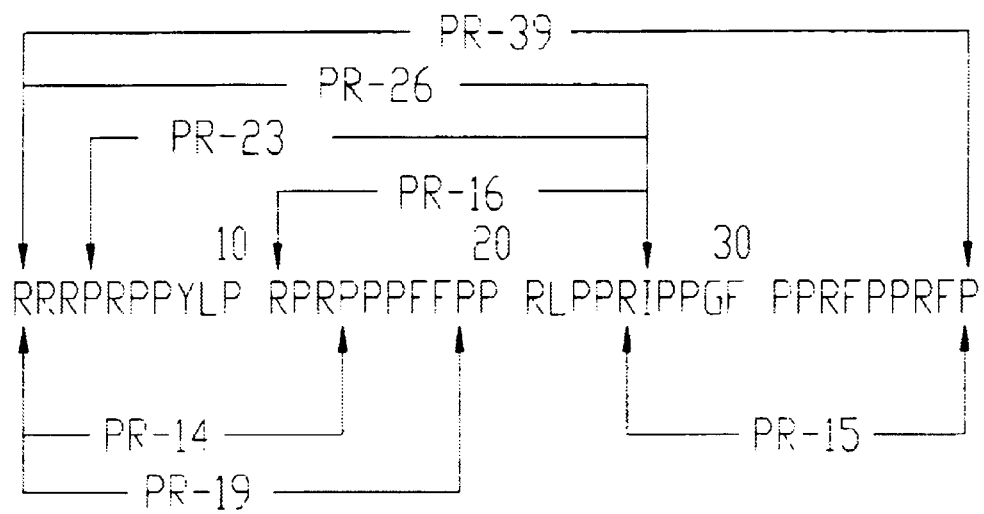
FIG. 1 is the amino acid sequence of PR-39 and various truncated analogs thereof, wherein the single letter amino acid code is used and the left side of the sequence is the $NH_2$-terminal end.

The following example illustrates the preferred practice of the invention. It is to be understood, however, that this example is provided by way of illustration only and nothing therein should be taken as a limitation upon the overall scope of the invention.

EXAMPLE

Materials and Methods

Peptide design and synthesis. Theoretical predictions of peptide characteristics, relative to hydrophilicity, hydrophobicity, and antigenicity, were accomplished using a computer software program (Peptide Companion, Peptide International, Louisville, Ky.). The following peptides were synthesized: PR-39, PR-26, PR-23, PR-19, PR-16, PR-15, and PR-14; the sequences of these peptides appear in the Sequence Listing as Sequence ID Nos. 1 through 7, respectively. Peptides were synthesized by the solid-phase method using t-Boc chemistry with an Applied Biosystems Model 431 Peptide Synthesizer (ABI, Foster City, Calif.). Amino acid derivatives having the L-configuration were used. Peptide purification and characterization were conducted as described previously (Shi et al., 1994b; Shi et al., 1996). Briefly, the peptides were purified on a reversed-phase high-performance liquid chromatography (RP-HPLC) system (Beckman Instruments, Fullerton, Calif.) with a Vydac 218 TP $C_{18}$ column (0.46×25 cm), analyzed by fast-atom mass spectrometry (AUTOSPEC-Q; VG Analytical Ltd., Manchester, United Kingdom), and visualized by acid-urea polyacrylamide gel electrophoresis (AU-PAGE). In the AU-PAGE analysis, peptides (10 μg) were dissolved in 20 μl of sample buffer (3M urea with 5% acetic acid) and the gels were run at 150V for approximately 15 min. or until the dye front (methyl green) had migrated to the end of the gel. The gel was stained with 0.3% amido black.

Antibacterial activity assays. Synthetic peptides were evaluated for antibacterial activity by previously described gel-overlay and "lawn-spotting" assays (Shi et al., 1994b), by determination of the minimal inhibitory concentrations (MICs) and the minimal bactericidal concentrations (MBCs) of PR-26 and PR-39, and by determination of the postantibiotic effect (PAE) of PR-26 and PR-39 and the bacterial susceptibility to neutrophil phagocytosis by PR-26 and PR-39.

(i) Gel-overlay assay. Peptides were subjected to AU-PAGE as described previously (Shi et al., 1994b). The acid-urea gels were overlaid with 10$^6$ bacteria (*E. coli*, ATCC 25922) in 3% tryptcase soy broth (TSB) and 1% agarose medium, and the overlaid gels then were incubated at 37° C. for 18 hr. Bactericidal activity was indicated by clear zones on the agarose gels.

(ii) Lawn-sooting assay. Lawns of bacteria (*E. coli*, ATTC 25922, or *S. typhimurium*, KSU isolate 7) were made on sheep-blood or brain-heart-infusion agar plates. After drying at room temperature for 10 min, 5 μl of the various peptides (dissolved in 0.01% acetic acid or phosphate buffered saline (PBS), pH 7.4) and a medium control were spotted on the surface of the bacterial lawn. Plates were incubated at 37° C. for 18 hr. Bactericidal activity was indicated by a clear zone on the bacterial lawn (Shi et al., 1994b).

(iii) MICs and MBCs. For peptides that showed antibacterial activity using the gel-overlay and lawn spotting assays, MICs and MBCs were determined by the microdilution broth method (NCCLS, 1990). Briefly, 50 µl of twofold serial dilutions (128 to 0.25 µM) of synthetic peptides were dispensed into wells of 96-well tissue culture plates. Bacteria (*E. coli*, ATCC 25922; *E. coli*, K88; *S. typhimurium*, fresh isolate from a dog; *Salmonella choleraesuis* ATCC 6962; *Streptococcus suis*, fresh isolate from porcine spleen; and *Staphylococcus aureus*) from sheep-blood or brain-heart-infusion agar plates were standardized to 0.5 McFarland in demineralized water using a radiometer/sensititre (Chelsea Instrument Ltd., England). The water/bacteria suspension (100 µl) was immediately transferred to 10 ml of cation-adjusted Muller-Hinton broth and 50 µl of the bacterial suspension then were added to each well of the microtiter plate. Plates were incubated for 20 hr. at 37° C. and MICs were determined. Ten microliters of bacterial suspensions in Muller-Hinton broth also were diluted to determine the actual bacterial concentration using standard colony forming unit (CFU) counting. After determination of the MICs, 10 µl of each bacteria-peptide suspension were plated on sheep-blood or brain-heart-infusion agar plates and incubated for 24 hr. at 37° C. to determine the MBCs. MBC was considered that peptide concentration that inhibited 99.9% of the original CFUs (NCCLS, 1990).

(iv) PAE. *S. typhimurium* was used to evaluate the PAE of PR-26 and PR-39. Stationary phase bacteria were adjusted to $5\times10^7$ bacteria/ml in brain-heart-infusion agar and incubated with different concentrations of PR-26 or PR-39 at 37° C. for 2 hr. Control tubes without PR-peptides were treated in an identical manner to the experimental tubes. PR-26 and PR-39 were removed by centrifugation (13,600×g for 1 min.) and 100 µl of the bacteria were resuspended in 0.9 ml of PR-peptide-free brain-heart-infusion agar and incubated at 37° C. Bacteria (20 µl) were diluted in sterile saline immediately after removal of the PR-peptides and then at hourly intervals, and 20 µl aliquots were spread on nutrient agar plates. Viable bacteria were counted. Tests were repeated on three different days. PAE was determined by calculating the difference in time required for the number of test and control bacteria to increase 1 $\log_{10}$ above the number present immediately after removal of PR-peptides from the test cultures. The results were expressed as the mean±standard deviation. A PAE greater than 30 min. was considered significant (MacKenzie and Gould, 1993).

(v) Susceptibility to neutrophil phagocytosis. Porcine neutrophils were isolated from 6 to 8 week-old-crossbred pigs by density-gradient centrifugation and hypotonic lysis as previously described (Shi et al., 1994a). *S. choleraesuis*, ATCC 6962 was used in this experiment. Bacteria were incubated with PR-26 or PR-39 for 10 min. at 37° C. Peptides were removed from the bacterial cultures by centrifugation at 13,600×g for 1 min. Bacteria were resuspended in 1 ml of PBS and 0.1 ml of bacteria was mixed with $2\times10^6$ porcine neutrophils. The final volume was adjusted to 0.5 ml, 15% porcine serum. Bacteria without neutrophils and neutrophils without bacteria were used as controls. Tubes were incubated at 37° C. in a reciprocating water bath at 110 oscillations/min. Aliquots of 50 µl from the experimental tubes were used to prepare slides using a Cytospin 2 centrifuge (Shandon Products Ltd., Pittsburgh, Pa.). Slides were stained with Leuko-Stat solutions (Fisher, Pittsburgh, Pa.). Phagocytosis was determined by light microscopy at a magnification of 1.000. At least 200 neutrophils were examined. The degree of phagocytosis was calculated according to the following formula: phagocytic index=(percentage of neutrophils containing at least one bacteria)×(mean number of bacteria per positive cell). Tests were repeated on three different days. Results were expressed as the mean±standard deviation.

Influence of PR-39 on neutrophil chemotaxis. Chemotaxis of porcine neutrophils was measured by the procedure of Salak et al. (1993). Briefly, PR-14, PR-15, PR-16, PR-26, or PR-39 (30 µl in Dulbecco's Modified Eagle's medium) were placed in the bottom chamber of a modified Boyden chamber (Neuro Probe, Cabin John, Md.) and porcine neutrophils (50 µl at $5\times10^6$ cells/ml) were placed in the top chamber. The chambers were incubated at 37° C. for 30 min. Cells that migrated through the porous membrane (pore size 5 µm) were stained using LeukoStat solution and enumerated. Five microscope fields were counted and the cells that migrated through the membrane were standardized to the medium control and referred to as the migration index.

Influence of PR-26 and PR-39 on intestinal epithelial cells. A nonradioactive assay based on the cellular conversion by viable cells of a tetrazolium salt into a blue formazan product was used to determine if PR-26 or PR-39 were toxic to intestinal epithelial cells. Ninety-six-well microtiter plates were seeded with the rat intestinal epithelial cell line, IEC6, ($5\times10^4$ cells/well) in DMEM containing 10% fetal bovine serum, 1% antibiotic/antimycotic, and 0.1 bovine insulin. and incubated at 37° C. for three days to achieve confluency. Cells then were incubated with different concentrations of PR-26 or PR-39 in medium without antibiotic/antimycotic for three days. Well contents then were aspirated and monolayers were washed with medium. Medium (100 µl) and 15 µl of dye solution (Promega, Madison, Wis.) were added to each well and plates were incubated for 4 hr. at 37° C. Solubilization buffer (100 µl, Promega, Madison, Wis.) was added to each well and plates were incubated overnight to allow solubilization of the formazan crystals. Absorbance then was read at 570 nm using a microplate reader.

Effect of PR-26 on survival of mice challenged with *S. typhimurium*. Three separate *S. typhimurium* challenge studies were conducted with mice. In the first experiment, 45 A/J mice (Jackson Labs, Bar Harbor, Me.) were orally challenged with *S. typhimurium*. Feed was withdrawn 4 hrs. prior to an oral inoculation. Twenty min. prior to the inoculation with *S. typhimurium* mice were given a 30 µl dose of a 10% sodium bicarbonate solution in PBS. *S. typhimurium*, strain KSU007, was started in brain heart infusion broth overnight and then grown for 6 hrs. in Luria Broth Base (GIBCO, Gaithersburg, Md.). After centrifugation, bacteria were suspended in a 1% gelatin solution (final concentration $1.24\times10^{10}$ *S. typhimurium*/ml), and then 25 µl were given orally. Immediately following oral inoculation with *S. typhimurium*, mice were given 0, 100, or 250 µg of PR-26 in PBS. A second dose of PR-26 or PBS was given 4 hrs. later.

In the second experiment, 45 Balb/C (Salmonella susceptible) mice were given i.p. injections of *S. typhimurium* ($2\times10^4$/ml) that had been grown as previously described, but resuspended in PBS. Mice then received either 0, 50, or 100 µg of PR-26 in 100 µl PBS i.p. immediately after the *S. typhimurium*.

In the third experiment, the efficacy of timing of delivery of PR-26 was evaluated. The protocol was the same as in the second experiment, except that only the 50 µg/mouse dose of PR-26 was used and the PR-26 was delivered immediately (time 0), or 24, 48, or 72 hrs. after the *S. typhimurium* injection. A control group received PBS at time 0. Fifteen mice were used in all treatments except the 72-hour treatment, which had 16.

Regulation of neutrophil production by PR-26 and PR-39.
 (i) $O_2^-$ production assays. Whole-cell $O_2^-$ production by porcine peripheral blood neutrophils was determined by the superoxide dismutase-inhibitable reduction of ferricytochrome c as previously described (Shi et al., 1994a). Cell-free $O_2^-$ production was measured as previously described (Leto et al., 1991) using 96-well plates and a Molecular Devices Thermomax microplate reader (Menlo Park, Calif.). Reactions (100 µl) contained $10^6$ cell equivalents of human neutrophil cytosol and $5 \times 10^5$ cell equivalents of deoxycholate-solubilized membranes prepared from human peripheral blood neutrophils. Reaction mixtures contained 50 mM potassium phosphate (pH 7), 0.2 mM acetylated cytochrome c, 4 mM $MgCl_2$, 1 mM EGTA, 10 µM FAD, 1 µM GTP-γS, and 200 µM NADPH. The reactions were initiated by addition of 40 µM arachidonic acid. Control reactions contained 5 µg of superoxide dismutase. Superoxide anion generation was calculated based on superoxide dismutase-inhibitable changes in cytochrome c absorbance observed at 551 nm. The reactions were followed for 20 min. after addition of arachidonic acid, with absorbance readings taken at 1-min. intervals. Maximum rates of superoxide generation were calculated from a linear least squares fit of 10 consecutive 1-min. data points. Determinations were based on reactions performed in duplicate.

(ii) Binding assays. Neutrophils were disrupted by sonication, and unbroken cells, debris, and granules were removed by centrifugation (13,000×g for 60 min.). Cytosol fractions were prepared by centrifugation (100,000 g for 45 min.) of the supernatants to remove residual membranes. Cytosolic proteins (15 µg in reducing buffer) were separated on a 7.5% SDS PAGE gel, transferred to PVDF membranes, and probed with biotinylated PR-39 (0.3 µM) for 2 hr. Binding between PR-39 and cytosolic proteins were visualized by a chemiluminescent streptavidin alkaline phosphatase system using an Epson scanner (Torrance, Calif.) and the NIH Image program. PR-39 was labeled with biotin hydrazide at the carboxy-terminus (Pierce Chemical Co., Rockford, Ill.) and purified by gel filtration chromatography.

Competitive ligand-blot assays were performed by incubating recombinant $p47^{phox}$ (0.02 µM) with or without various concentrations (0.006, 0.06, and 0.6 µM) of PR-39 for 1 hr. at 37° C. and then with biotinylated PR-39 (0.06 µM) for an additional 1 hr. at 37° C. The solutions were dialyzed against $ddH_2O$ for 1 hr. at 4° C. before blotting to nitrocellulose (5 µl) and detection with a streptavidin alkaline-phosphatase detection system as described above.

Methods for production of the glutathione S-transferase (GST)-$p47^{phox}$-SH3 (residues 151–284) fusion protein have been previously described (Leto et al., 1994). For solution binding assays, lysates of recombinant $p22^{phox}$ protein (residues 127–195) from baculovirus-infected cells ($2.5 \times 10^4$ cell equivalents per assay) were mixed with peptides and incubated for 1 hr. at 20° C. with 100 µl of GST-$p47^{phox}$ bound to glutathione-Sepharose beads (15% suspension). Bound proteins were washed three times in 15 volumes of ice-cold 100 mM KCl/3 mM NaCl/3.5 mM $MgCl_2$/0.15 mM phenylmethanesulfonyl fluoride/10 mM Pipes (pH 7.5), eluted with 1% SDS, and analyzed by SDS-PAGE followed by immunoblotting with mouse anti-$p22^{phox}$ antibody (mAb 449; A. Verhoeven, Central Laboratories of the Netherlands Red Cross). Controls included blotting of recombinant $p22^{phox}$ lysate ($5 \times 10^3$ cell equivalents) alone (p22) and bound complexes detected without competing PR peptides (−).

Results and Discussion

Figure 2:
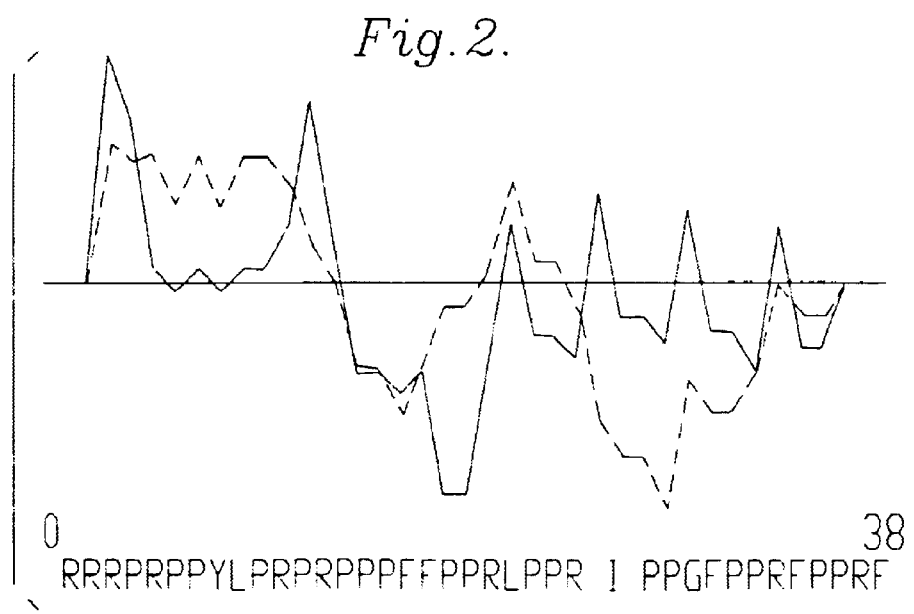
FIG. 2 is a protein hydrophilicity (solid line) and antigenicity (dashed line) plot for PR-39 wherein the hydrophilic and antigenic domains are above the horizontal line and the hydrophobic domains are below the horizontal line.

Peptide design and synthesis. PR-39 and six analogs were synthesized and named PR-39 (whole molecule), PR-26 ($NH_2$-terminal segment 1 to 26), PR-23 (control segment 4 to 26), PR-19 ($NH_2$-terminal segment 1 to 19), PR-16 (central segment 11 to 26). PR-15 (COOH-terminal segment 25 to 39), and PR-14 ($NH_2$-terminal segment 1 to 14). Peptide sequences are illustrated in FIG. 1. Rationale for design of the peptides was based on the graphic protein hydrophilicity scale (FIG. 2), since the hydrophilicity profile indicates locations of important interaction sites such as antibody and receptor binding sites (Hopp, 1985). PR-26 was designed to mimic the hydrophilicity profile of PR-39 which has a hydrophilic $NH_2$-terminus and a hydrophobic COOH-terminus. As most endogenous antibacterial peptides are cationic molecules, PR-14, the highest positively charged segment (43% vs. 25% of whole molecule), was designed to test if cationicity itself was enough for antibacterial activity. The central domain, PR-16, having the average positive charge intensity (25%) was synthesized as the control for PR-14. PR-15, the COOH-terminus of PR-39 was designed to determine if it was one of the functional domains of PR-39. PR-23 was designed to evaluated the importance of the first three arginine residues of PR-26. PR-19 was designed to assess the contribution of the COOH-terminus to the activity of PR-26.

Figures 3, 4:
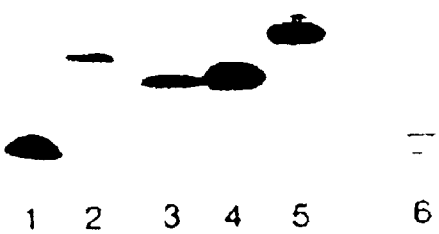
FIG. 3 is a photograph of an AU-PAGE analysis of synthetic peptides wherein each lane contains ten micrograms of peptide; lane 1=PR-14; lane 2=PR-15; lane 3=PR-16; lane 4=PR-26; lane 5=PR-39; and lane 6=neutrophil granule extract, with calculated molecular weights ($MW_{cal}$) over the experimental mass spectrometry data ($MW_{exp}$) listed above each lane for the respective synthetic peptides.
FIG. 4 is a photograph of the gel shown in FIG. 3 after being subjected to a gel-overlay assay, wherein the clear zones indicate antibacterial activity.

Calculated molecular weights and experimental determinations of the mass of synthetic peptides suggested that these peptides possessed the designed sequences (1813, 1777, 1939, 3230, and 4720 calculated molecular weight vs 1812, 1777, 1941, 3230, and 4720 experimental determination of mass for PR-14, PR-15, PR-16, PR-26, and PR-39, respectively). Synthetic peptides (>95% purity in RP-HPLC) were subjected to AU-PAGE to further determine the purity and charge intensity. FIG. 3 shows the results of this analysis for PR-14, PR-15, PR-16, PR-26, and PR-39 (data not shown for PR-19 and PR-23). As expected, PR-14 migrated in the front since it has the highest positive charge intensity; PR-15, having the lowest positive charge intensity, migrated far behind PR-14 even though its mass is slightly less than PR-14. Because PR-16 and PR-26 are smaller molecules than PR-39, they migrated faster than the parent molecule. Native PR-39 and synthetic PR-39 behaved identically in AU-PAGE and RP-HPLC analyses (data not shown).

Figure 5:
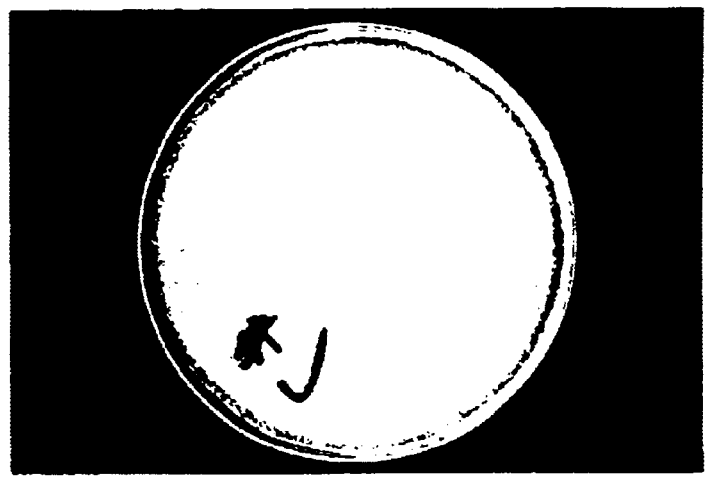
FIG. 5 is a photograph of an agar plate showing the results of an antibacterial "lawn-spotting" assay using *Salmonella typhimurium* wherein the spot positions are numbered on the left of the photograph; position 1=medium control (0.01% acetic acid); positions 2, 3, and 4=PR-14, PR-15, and PR-16, respectively, at 1 mg/ml in 0.01% acetic acid; positions 5 and 6=100 μmoles and 50 μmoles, respectively, of PR-26 in phosphate buffer saline, pH 7.4; positions 7, 8, 9, and 10=100, 50, 25, and 10 μmoles, respectively, of PR-26 in 0.01% acetic acid; and positions 11, 12, and 13=100 μmoles, 50 μmoles, and 25 μmoles, respectively, of PR-39 in 0.01% acetic acid.

Antibacterial Activity Assays.
 (i) Gel-overlay assay. In the gel-overlay bactericidal assay, only PR-26 and PR-39 were found to have antibacterial activity against *E. coli*. FIG. 4 shows the results of this assay for PR-14, PR-15, PR-16, PR-26, and PR-39 (data not shown for PR-19 and PR-23).
 (ii) Lawn-spotting assay. In the "lawn-spotting" antibacterial assay, PR-14, PR-15, PR-16, PR-19, PR-23, PR-26, and PR-39, and the combination of PR-14, PR-15, and PR-16, were tested. FIG. 5 shows the results of this assay for PR-14, PR-15, PR-16, PR-26, and PR-39 (data not shown for PR-19, PR-23, and the combination of PR-14, PR-15, and PR-16). Only PR-26 and PR-39 had antibacterial activity. All of the other segments and their mixtures showed no antibacterial activity even at 1 mg/ml.

These results suggest that: 1) the very cationic $NH_2$-terminus of PR-39 is not sufficient for antibacterial activity; 2) the COOH-terminal segment 27 to 39 does not contribute to the antibacterial activity of PR-39; 3) PR-26, the $NH_2$-terminal segment 1 to 26, contains the antibacterial domain of PR-39; 4) the $NH_2$-terminal segment 1 to 3 is essential for antibacterial activity; (5) the COOH-terminal segment 20 to 26 is essential for antibacterial activity; and 6) certain secondary structure conformation is required for the antibacterial activity of PR-26 and PR-39 since segment mixtures did not have any antibacterial activity. The "lawn-spotting" assay also showed that PR-26 had greater antibacterial activity against *E. coli* and *S. typhimurium* than PR-39 (FIG. 5).

Figure 6:
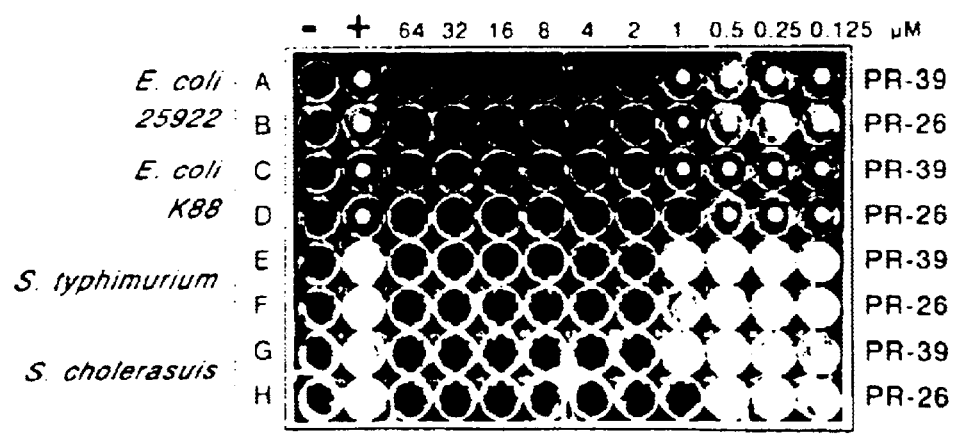
FIG. 6 is a photograph of a 96-well microtiter plate used to determine the minimal inhibitory concentrations of PR-26 and PR-39 against enteric bacteria.

(iii) MICs and MBCs. The MICs of PR-26 and PR-39 for *E. coli*, 25922; *E. coli*, K88; *S. typhimurium*; *S. choleraesuis*; *S. suis*; and *S. aureus* are shown in FIG. 6 and Table 1. For the enteric, Gram-negative bacteria, the MICs of PR-26 and PR-39 ranged from 1 to 4 $\mu$M; PR-26 had a lower MIC than PR-39. Similarly, the MBCs of PR-26 were the same or lower than the MBCs of PR-39 and ranged from 2 to 8 $\mu$M for the Gram-negative bacteria (Table 1). These findings suggest that PR-26 may be an effective antibiotic against enterdc Gram-negative bacteria such as *E. coli* or Salmonella.

TABLE 1

MICs ($\mu$M) and MBCs ($\mu$M) of PR-39 and PR-26 against six strains of bacteria.

| Bacteria | MIC PR-39 | MIC PR-26 | MBC PR-39 | MBC PR-26 |
| --- | --- | --- | --- | --- |
| *Escherichia coli*. 25922 | 4 | 2 | 8 | 8 |
| *Escherichia coli*. K88 | 2 | 1 | 4 | 4 |
| *Salmonella typhimurium* | 4 | 2 | 4 | 2 |
| *Salmonella choleraesuis* | 2 | 1 | 4 | 2 |
| *Streptococcus suis* | >64 | 16 | >64 | >64 |
| *Staphylococcus aureus* | >250 | >250 | ND* | ND* |

Figure 7:
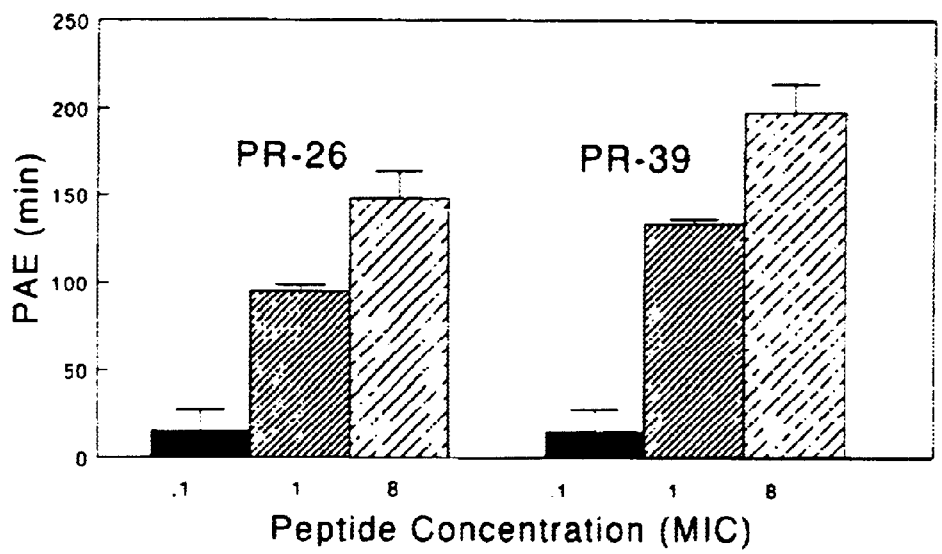
FIG. 7 is a graph illustrating the postantibiotic effect of PR-26 and PR-39 against *S. typhimurium*.

*Not determined (iv) PAE. The relationship between peptide concentration and the duration of PAE of PR-26 and PR-39 is shown in FIG. 7. Suboptimal peptide concentrations (0.1 MIC) only caused a slight growth delay in both PR-26- and PR-39-treated bacteria. However, at 1 and 8 MICs, PAEs against *S. typhimurium* were significantly increased. These findings agree with other antibacterial data and show clearly that PR-26 limits the growth of enteric bacteria.

Figure 8:
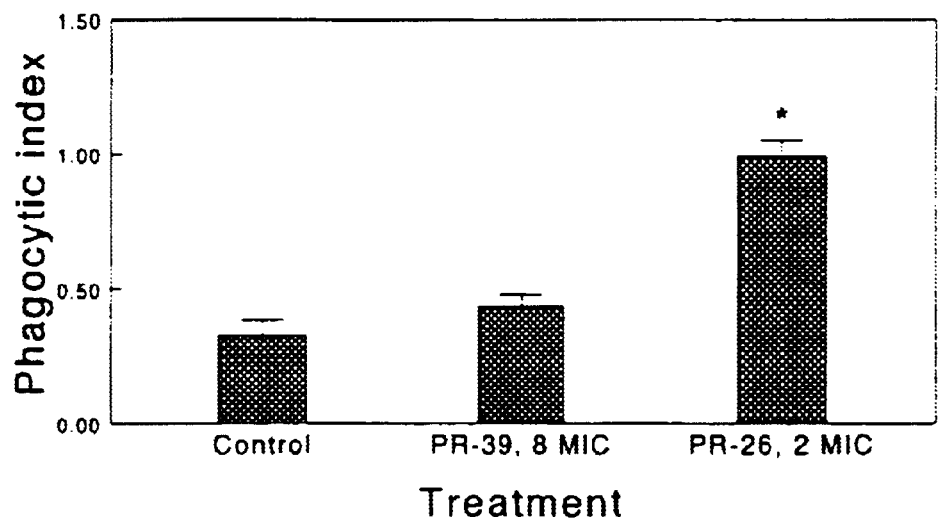
FIG. 8 is a graph illustrating the phagocytic susceptibility of *S. choleraesuis* after exposure to PR-26 and PR-39.

(v) Susceptibility to neutrophil phagocytosis. Bacteria treated with PR-26 were more susceptible to neutrophil phagocytosis (FIG. 8; PR-26 was different from control, P<0.05). A 10 min. exposure of *S. choleraesuis* to 2 MICs of PR-26 significantly increased the capability of porcine neutrophils to phagocytose the bacteria. Treatment of *S. choleraesuis* with PR-39 at 8 MICs did not increase the phagocytic index of porcine neutrophils. Neutrophils phagocytosed both single and filamentous bacteria. These data show that, in addition to the direct antibacterial activity of PR-26, this antibacterial peptide predisposes enteric bacteria to elimination by phagocytic cells. This property suggests that PR-26 works synergistically with the host's immune system to limit enteric bacterial growth.

Figure 9:
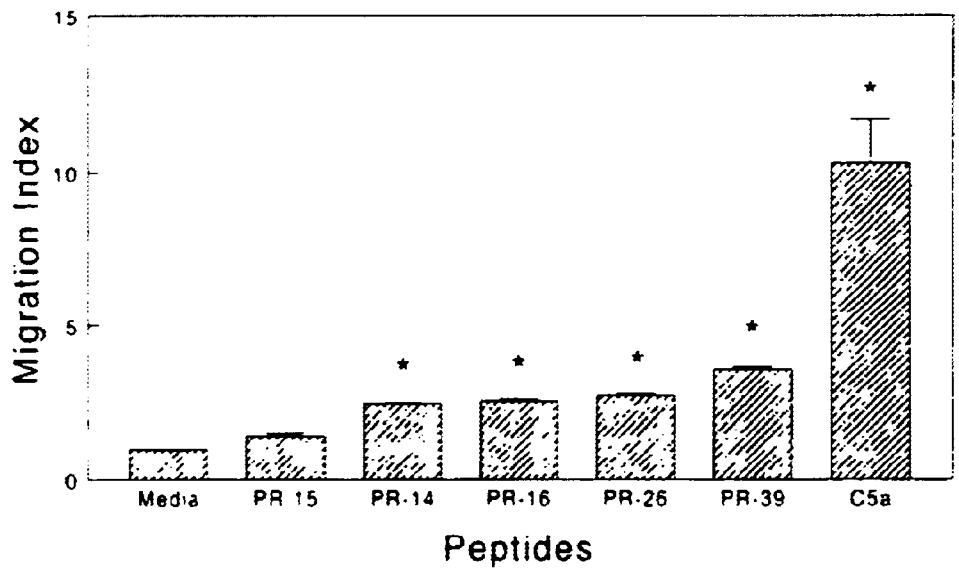
FIG. 9 is a graph illustrating the chemotaxis of porcine neutrophils by PR-39 and analogs thereof.
Figure 10:
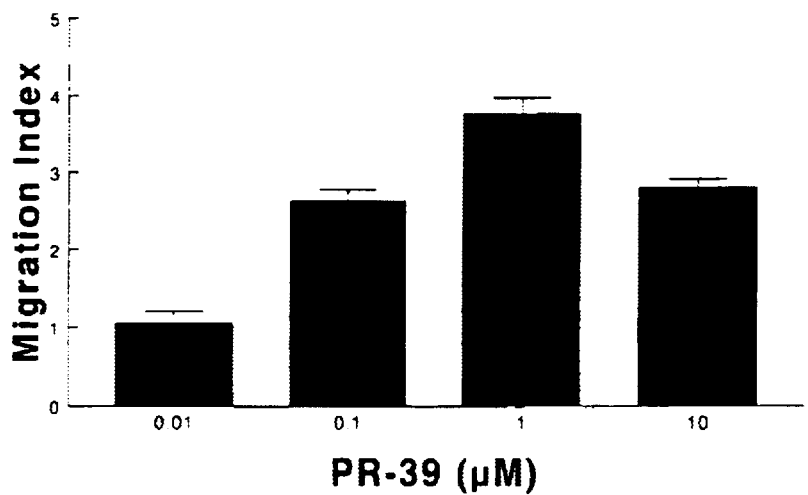
FIG. 10 is a graph illustrating a dose response of PR-39 for neutrophil chemotaxis.

Influence of PR-39 on neutrophil chemotaxis. Phagocytic cells migrate from the blood to areas of inflammation in response to chemotactic agents. FIG. 9 shows that PR-14, PR-15, PR-16, PR-26, and PR-39 are chemotactic agents for neutrophils (PR-14, PR-15, PR-16, and PR-26 are used at 1 $\mu$M, and PR-39 was used at 0.05 $\mu$M; the chemoattractant C5a, a positive control, was used at $1 \times 10^{-8}$M; starred entries are different from the control, P<0.05). FIG. 10 shows a dose response of PR-39 for neutrophil chemotaxis. The ability of PR-39 to function as a chemotactic agent increases the probability that sufficient phagocytic cells are present at an inflammatory site to limit an infection.

Figure 11:
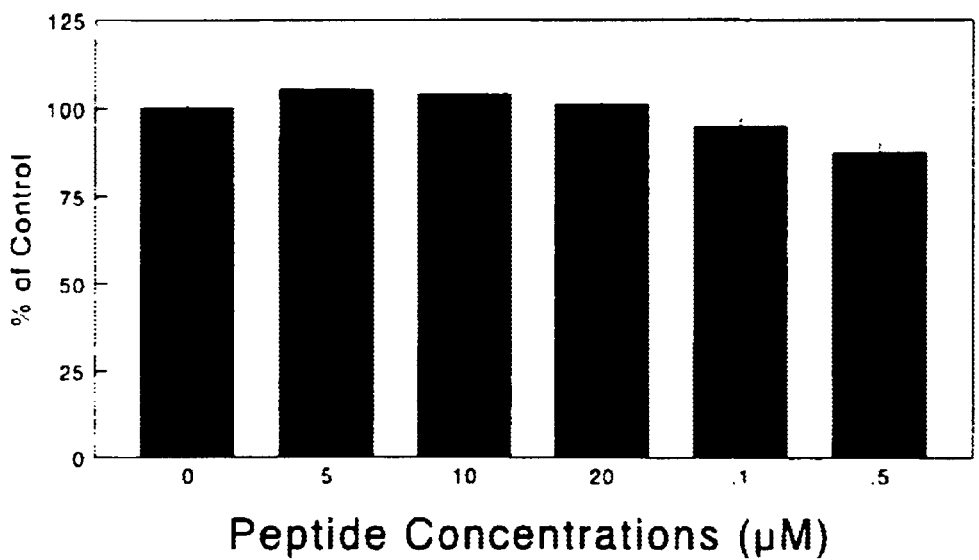
FIG. 11 is a graph illustrating the cytotoxicity of PR-26 and PR-39 in intestinal epithelial cells.

Influence of PR-26 and PR-39 on intestinal epithelial cells. FIG. 11 shows the cytotoxic activity of PR-26 and PR-39 on rat small-intestine epithelial cells (IEC-6). PR-26 was not cytotoxic to IEC-6 cells even at concentrations (20 $\mu$M) much greater than the MIC for this peptide. However, IEC-6 cells were sensitive to PR-39 as cytotoxicity occurred at 0.5 $\mu$M, which is lower than the MIC for this peptide. These data show that PR-26 does not damage cells of the small intestine and should, therefore, be a safe oral antibiotic.

Figure 12:
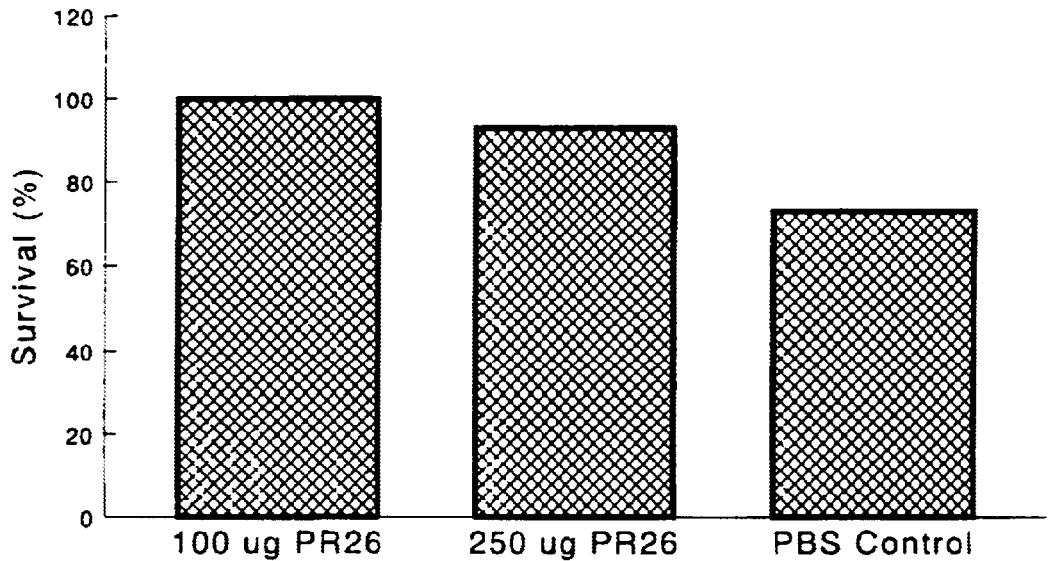
FIG. 12 is a graph illustrating percent survival of A/J mice 15 days after an oral challenge with *S. typhimurium* followed with 0, 100, or 250 μg PR-26.
Figure 13:
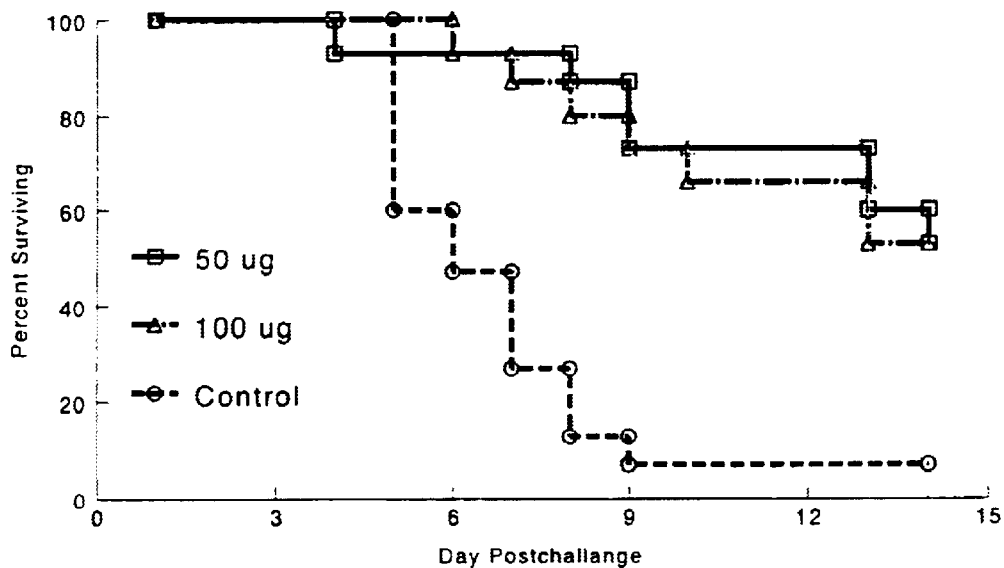
FIG. 13 is a graph illustrating survival of mice infected with *S. typhimurium* intraperitonealy (i.p.) followed with 0, 50, or 100 μg PR-26.
Figure 14:
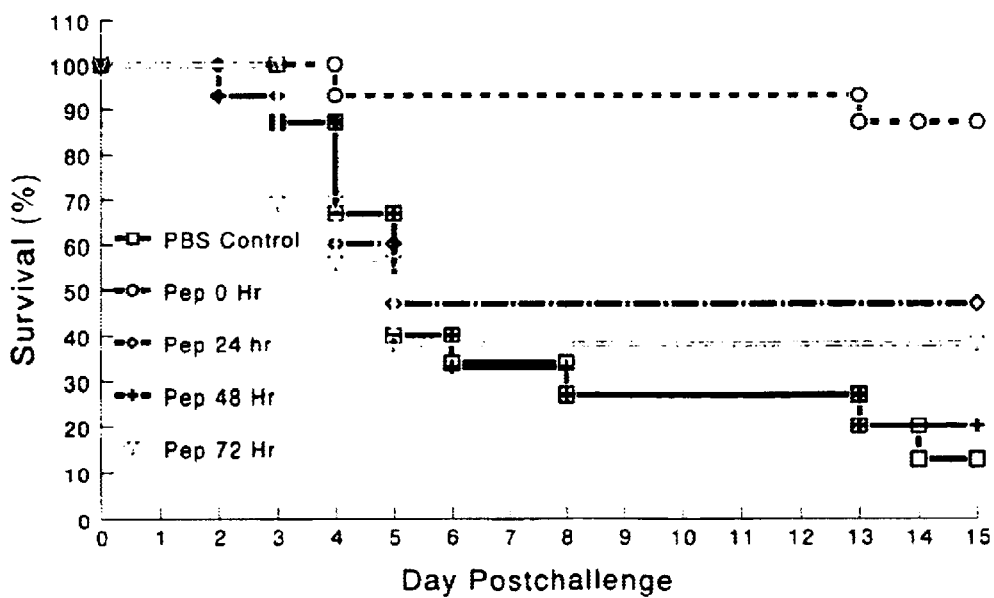
FIG. 14 is a graph illustrating survival of mice infected with *S. typhimurium* i.p. followed with 50 μg PR-26 at time 0, 24, 48, or 72 hours post-infection.

Effect of PR-26 on survival of mice challenged with *S. typhimurium*. In the first experiment, mice that received PR-26 were resistant to Salmonella (0 and 1 death for 250 and 100 $\mu$g/mouse, respectively), but the control group had a 27% mortality rate (FIG. 12; both PR-26 treatments were significantly different from controls, P<0.05). Based on these data, PR-26 was effective in increasing the survival rates in this Salmonella-resistant strain of mice. There was no evidence of toxicity caused by PR-26. In the second experiment, both 50 and 100 $\mu$g PR-26 were sufficient to increase survival to more than 50% at 14 days post-infection (FIG. 13; both PR-26 treatments were different from the PBS control at days 6 through 14, P<0.05, but not different from each other. In the third experiment, administration of PR-26 was most effective when given at time 0; however, the 24-hour post-infection treatment slightly improved the survival compared to the PBS treatment by day 14 (FIG. 14; treatments at 0, 24, and 72 hrs. were different from PBS control at day 15, P<0.05 for treatments at 0 and 24 hrs., P<0.10 for treatment at 72 hrs.). The delivery of PR-26 at 48 hrs. post-infection was not different than the PBS control treatment. The rapidity of uptake of *S. typhimurium* and delivery to the liver and spleen during an i.p. infection may be the cause of the reduced effectiveness of PR-26 by 48 hrs. post-infection.

Regulation of neutrophil $O_2^-$ production by PR-26 and PR-39.

Figure 15:
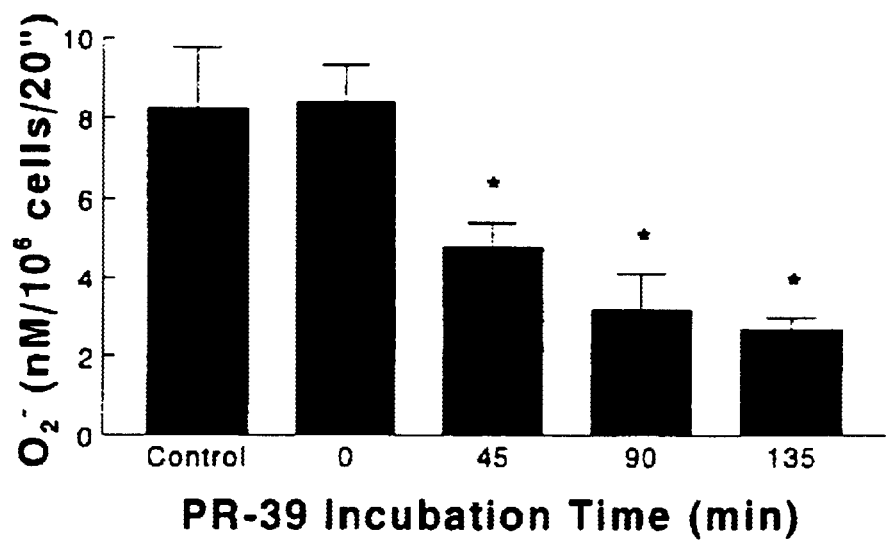
FIG. 15 is a graph illustrating that inhibition of whole-cell NADPH oxidase activity requires preincubation with PR-39.
Figure 16:
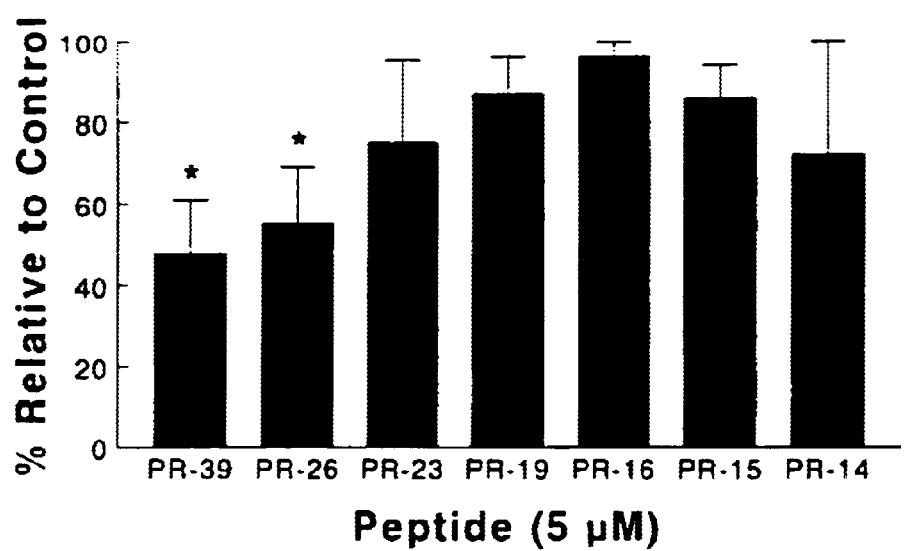
FIG. 16 is a graph illustrating whole-cell NADPH oxidase inhibition by PR-39 and analogs thereof.

(i) $O_2^-$ production assays. When PR-39 was incubated with neutrophils for at least 45 min. before simulation with phorbol myristate acetate (PMA), a significant reduction in 02 generation was observed (FIG. 15; neutrophils ($1 \times 10^6$) were incubated without (Control) or with PR-39 (5 $\mu$M) for the indicated times before stimulation with PMA; values are means±SEM, n=2; starred entries are different from control, P<0.05). This effect was even more apparent with longer pre-incubation periods, approaching as much as 70% oxidase inhibition. PR-26 also significantly reduced $O_2^-$ generation (FIG. 16; neutrophils were incubated with PR-39 or derivatives for 150 min. before stimulation with PMA; results are reported as % relative to control (no peptides); however, the statistical analysis was based on nmoles of $O_2^-$ produced; values are means, n=3; starred entries are different from control, P<0.05; this experiment was conducted twice with similar results). However, the shorter peptides, PR-14, PR-15, PR-16, PR-19, and PR-23, did not significantly reduce $O_2^-$ generation by intact neutrophils. PR-39 (20 μM) added to neutrophils at the same time as PMA activities did not affect generation of $O_2^-$, while longer incubation periods with this peptide did not affect neutrophil viability, as judged by trypan blue dye exclusion.

To investigate the inhibition of neutrophil $O_2^-$ generation by PR-39 and its fragments in more detail, a cell-free assay system of $O_2^-$ generation was used. PR-26 and PR-39 were very potent inhibitors of $O_2^-$ generation in the cell-free assay; concentrations that inhibited 50% ($IC_{50}$) of $O_2^-$ generation were approximately 1 and 2 μM, respectively (FIG. 17; data are the average of duplicate reactions and are representative of 3 to 4 independent experiments; control (100%) activities ranged from 0.9 to 2.4 nmol $O_2^-$ min/5× $10^5$ cell equivalents of membrane). At concentrations greater than 5 μM, both proline-rich peptides completely inhibited the generation of $O_2^-$. PR-15 and PR-16 did not affect $O_2^-$ generation; however, PR-14 did reduce $O_2^-$ generation at concentrations greater than 25 μM.

Figure 17:
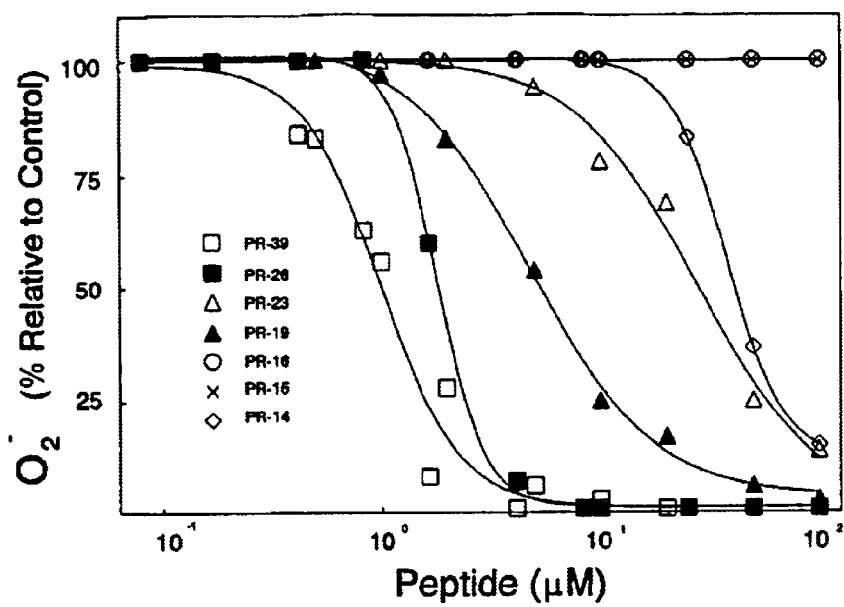
FIG. 17 is a graph illustrating cell-free NADPH oxidase inhibition by PR-39 and analogs thereof.

PR-19 and PR-23 had some oxidase inhibitory activity; $IC_{50}$'s of PR-19 and PR-23 were approximately 5 μM and 25 μM, respectively (FIG. 17). These findings suggest that both peptides contain the oxidase inhibitory domain, although the first three arginine residues of PR-26 contribute greatly to oxidase inhibitory activity.

(ii) Binding assays. The findings that PR-26 and PR-39 inhibited both cell-free and whole cell $O_2^-$ production by neutrophils and that inhibition required preincubation of cells with peptides for at least 45 min. prior to PMA stimulation suggested that these peptides act through some intracellular target, such as the NADPH oxidase components themselves. To determine if PR-39 bound to specific neutrophil cytosol components, human and porcine cytosolic proteins were separated by SDS-PAGE, transferred to a PVDF membrane, and probed with biotinylated PR-39. Using this ligand-blot binding assay, it was found that PR-39 bound to a 47 kDa protein in both human and porcine cytosol preparations (FIG. 18; cytosolic protein (50 μg) from human and porcine polymorphonuclear (hPMN and pPMN) leukocytes was subjected to SDS-PAGE, transferred to a PVDF membrane, and then probed with biotinylated PR-39; molecular masses of standards in kDa are shown on the left of the blots).

Figure 19:
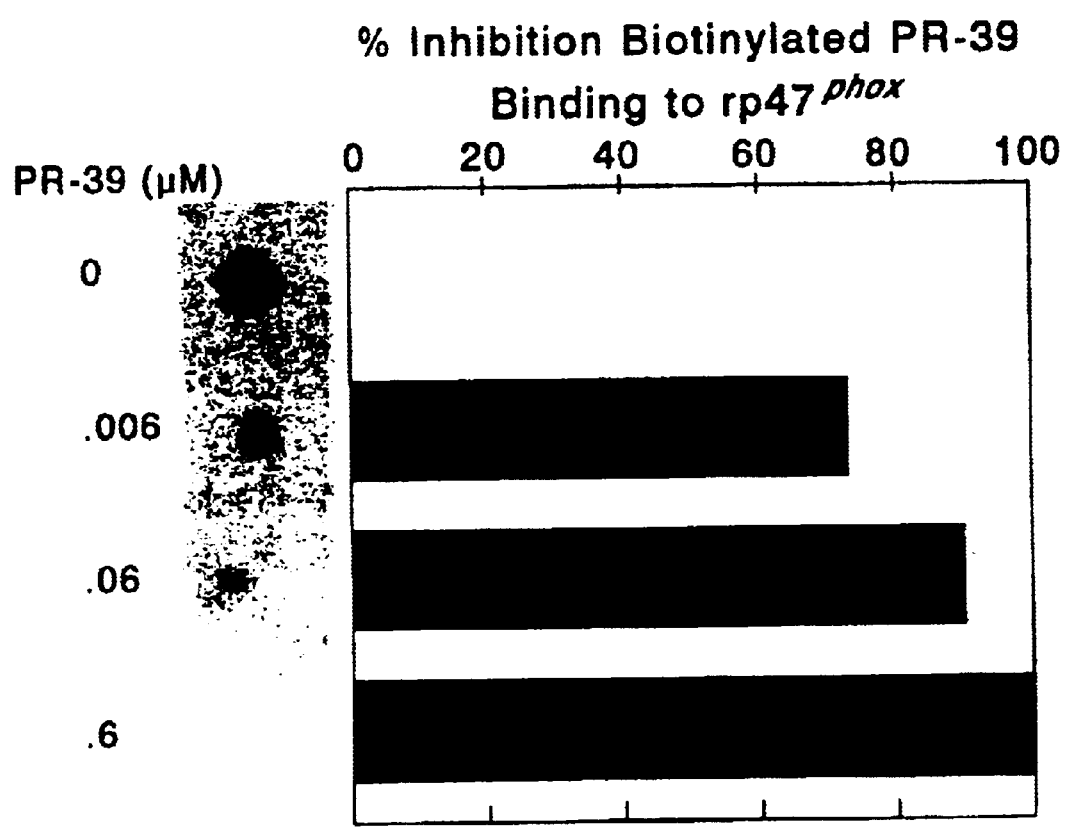
FIG. 19 is a photograph of a blot and a corresponding graph illustrating the binding of PR-39 to recombinant p47$^{phox}$.

Competitive binding assays were conducted to determine if PR-39 bound to recombinant $p47^{phox}$. These solution binding experiments with pure recombinant $p47^{phox}$ and PR-39 showed that increasing concentrations of nonbiotinylated PR-39 inhibited specific binding of biotinylated PR-39 to recombinant $p47^{phox}$ (FIG. 19; competitive binding analysis was conducted by incubating various concentrations of PR-39 with recombinant $p47^{phox}$ and then with biotinylated PR-39; after dialysis, solutions were dot-blotted onto PVDF membranes and probed for bound biotinylated PR-39). Binding was inhibited 90% at equimolar concentrations of labeled and unlabeled peptide (0.06 μM) and was completely blocked by a tenfold excess of unlabeled peptide. This finding shows that PR-39 binds to $p47^{phox}$, that binding is specific, and implies that PR-39 decreases $O_2^-$ generation by interfering with this cytosolic component of the NADPH oxidase complex.

Figure 18:
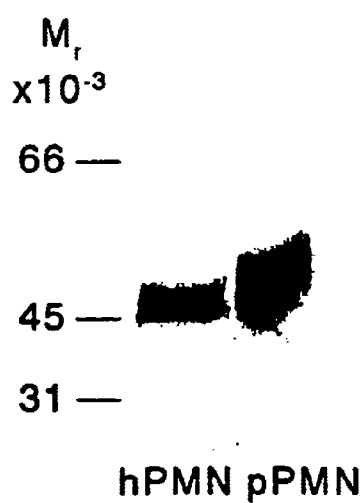
FIG. 18 is a photograph of blots illustrating the binding of biotinylated PR-39 to a 47 kDa neutrophil cytosol protein.

At least two proline-rich sequences, the COOH-terminal region (residues 358–371) of $p47^{phox}$ and the cytoplasmic region (residues 149–162) of $p22^{phox}$, are thought to bind to SH3 domains of $p67^{phox}$ and $p47^{phox}$, respectively, and are essential for the activation of NADPH oxidase in vivo (Leto et al., 1994; Sumimoto et al., 1994; Finan et al., 1994; McPhail, 1994; de Mendex et al., 1996). Data obtained by probing neutrophil cytosolic proteins with biotinylated PR-39 suggested that PR-39 did not bind to $p67^{phox}$ (FIG. 18). Because PR-39 bound directly to $p47^{phox}$, it was reasoned that PR-39 could interfere with assembly of NADPH oxidase by blocking its interaction with $p22^{phox}$.

Figure 20:
FIG. 20 is a photograph of blots illustrating the degrees to which PR-26 and PR-39 block the interaction between GST-p47$^{phox}$ and recombinant p22$^{phox}$.
Figure 21:
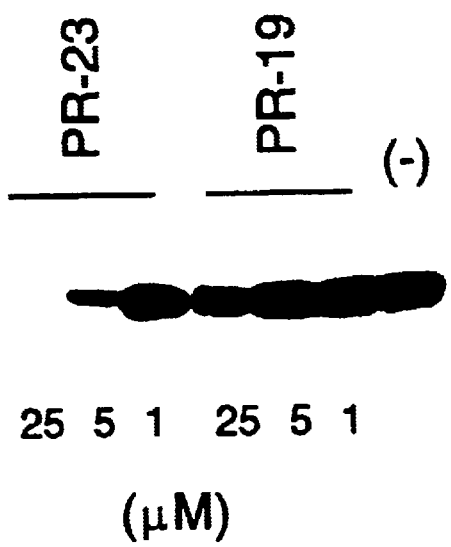
FIG. 21 is a photograph of a blot illustrating the degrees to which PR-19 and PR-23 block the interaction between GST-p47$^{phox}$ and recombinant p22$^{phox}$.
Figure 22:
FIG. 22 is a photograph of a blot illustrating the degrees to which PR-14, PR-15, PR-16, and PR-26 block the interaction between GST-p47$^{phox}$ and recombinant p22$^{phox}$.

To examine this hypothesis, solution binding assays were conducted between GST-$p47^{phox}$ SH3 domain fusion protein and a recombinant $p22^{phox}$ cytoplasmic domain (residues 127–195) in the presence or absence of PR-39 or its derived fragments. PR-26 and PR-39 effectively blocked the interaction between GST-$p47^{phox}$ and recombinant $p22^{phox}$ at concentrations close to their $IC_{50}$'s observed in the cell-free oxidase assay (FIG. 20; PR-26 or PR-39 were mixed with recombinant $p22^{phox}$ and incubated for 60 min. with GST-$p47^{phox}$-SH3 fusion proteins (0.5 μg) bound to glutathione-Sepharose beads and analyzed as described: after SDS-PAGE, Sepharosebound proteins were analyzed by immunoblotting with anti-$p22^{phox}$ antibody; controls included blotting of recombinant $p22^{phox}$ lysate (5×$10^3$ cell equivalents) alone (p22) and bound complexes detected without competing PR-peptides (–); concentrations of competing peptides defined above each blot are indicated below the blots). Using this binding assay, analysis of the inhibition by PR-14, PR-15, PR-16, PR-19, and PR-23 revealed the importance of the COOH-terminal region of PR-26 in SH3 binding (FIG. 21; inhibition by PR-19 or PR-23, conducted as in FIG. 20) (FIG. 22; comparison of inhibitory activities of smaller peptides at 25 μM). These data not only supported the hypothesis that PR-39 blocks the interaction between $p47^{phox}$ and $p22^{phox}$, but also indicated that the main structural motif involved in the interaction between PR-39 and SH3 domains of $p47^{phox}$ was in the central segment (PR-16) of PR-39. This 16-residue segment contains structural elements compatible with consensus features of both classes of SH3 peptide ligands (Feng et al., 1994; Lim et al., 1994).

Two sequences within PR-16, RPPPFFP (Sequence ID No. 8) and PPRLPPRI (Sequence ID No. 9), conform to consensus sequences for either Class I (+) and Class II (–) binding orientations, $X_1pX_2PpX_3P$ and $X_3,PpX_2,PpX_1,$, respectively (upper-case denotes critical contact residues, P denotes proline, and $X_1$ or $X_{1'}$ favor arginine residues). Since PR-23 inhibits better than PR-19, a Class II binding orientation appears likely. However, because PR-19 had greater inhibitory activity in the cell-free assay but was less potent in blocking the interaction of $p47^{phox}$ SH3 domains with $p22^{phox}$ when compared to PR-23, the polybasic motif of the amino-terminus of PR-26 also represents a separate important component of oxidase inhibition. This observation is supported by studies showing that several other cationic peptides effectively inhibit NADPH oxidase, including peptides derived from $p47^{phox}$ (Joseph et al., 1994). Thus, critical regions at both ends of PR-26 have been defined based on dramatic losses of function seen with the deleted forms, PR-19 and PR-23.

The polybasic motif at the amino-terminus of PR-26 and PR-39, in addition to their overall amphiphatic character, may have a role in promoting internalization of these inhibitory peptides, since similar structural properties are thought to enable internalization of various synthetic peptides designed for intracellular targets (Derossi et al., 1994;

Mann et al., 1994; Fawell et al., 1994; Vellette et al., 1994; Taffs et al., 1992). PR-39 uptake may involve an active endocytic process or direct membrane lipid interactions, since this peptide binds and induces conductance changes in pure lipid bilayers (Cabiaux et al., 1992).

PR-39 is the first naturally occurring down regulator of phagocyte NADPH oxidase identified that interferes with assembly of this enzyme by binding to p47$^{phox}$. Little is known about the mechanisms governing respiratory burst kinetics, although models based on a continuous cycling of cytosolic components are consistent with the direct inhibitory effects of PR-39 on oxidase component interactions. The paradoxical finding of a neutrophil peptide possessing both antibacterial and oxidase inhibitory activities is intriguing, since a switch from oxygenependent to oxygen-independent bactericidal mechanisms by an accumulation of this peptide within inflammatory sites could serve several important functions.

PR-39, which has a well-documented role as an antibacterial peptide, might have several roles in tissue repair by directly inhibiting NADPH oxidase activity and limiting related proinflammatory responses, while also affecting gene expression patterns that promote wound healing (Gallo et al., 1994). Furthermore, since reactive oxygen intermediates have also been shown to function as second messengers that can regulate gene expression (Schreck et al., 1991), PR-39 may indirectly influence gene expression patterns related to oxidative stress. These opposing activities of PR-39 illustrate a fine balance required in host defense mechanisms: antibacterial activity is necessary to control microbial pathogens and oxidase inhibitory activity is important for restricting tissue damage caused by excessive oxygen radicals generated by NADPH oxidase. In the case of PR-39, one peptide possesses both activities. These findings suggest a mechanism for interaction between oxidative and nonoxidative antimicrobial systems of neutrophils and may serve as a basis for design of drugs effective against production of oxidants in chronic or acute inflammatory disease states.

REFERENCES

The following references are incorporated by reference herein.

Abo, A., Boyhan, A., West, I., Thrasher, A. J. & Segal, A. W. (1992) *J. Biol. Chem.* 267, 16767–16770.

Agerberth, B., Lee, J. Y. Bergman, T., Boman. H. G. Mutt, V. & Tornvall, H. (1991) *Eur. J. Biochem.* 202, 849–854.

Boman, H. G. (1991) *Cell* 65, 205–207.

Boman, H. G. (1995) *Annu. Rev. Immunol.* 13,61–92.

Boman, H. G., Agerberth, B. & Boman, A. (1993) *Infect. Immun.* 61, 2978–2984.

Cabiaux, V., Agerberth, B., Johansson, J., Homblé, F., Goormaghtigh, E. & Ruysschaert, J.-M. (1994) *Eur. J. Biochem.*, 224, 1019–1027.

DeLeo, F. R., Nauseef, W. M., Jesaitis, A. J., Burritt, J. B., Clark, R. A. & Quinn, M. T. (1995) *J. Bio. Chem.* 270, 26246–26251.

de Mendez, I., Adams, A. G., Sokolic, R. A., Malech, H. L. & Leto, T. L. (1996) *EMBO J.*, in press.

Demling, R. H. (1990) *Circ. Shock* 30, 297–309.

Derossi, D., Joliot, A. H., Chassaing, G. & Prochiantz, A. (1994) *J. Bio. Chem.* 269, 10444–10450.

Fawell, S., Seery, J., Daikh, Y., Moore, C., Chen, L. L., Pepinsky, B. & Barsoum, J. (1994) *Proc. Natl. Acad. Sci. USA* 91, 664–668.

Feng, S., Chen, J. K., Yu. H., Simon, J. A. & Schreiber, S. L. (1994) *Science* 266, 1241–1247.

Finan, P., Shimizu, Y., Gout, I., Hsuan. J., Truong, O., Butcher, C., Bennett, P., Waterfield, M. D. & Kellie; S. (1994) *J. Biol. Chem.* 269, 13752–13755.

Gabay, J. E. (1994) *Science* 264, 373–374.

Gallo, R. L., Ono, M., Povsic, T., Page, C., Eriksson, E., Klagsbrun, M. & Bernfield, M. (1994) *Proc. Natl. Acad. Sci. USA* 91, 11035–11039.

Gennaro, R., Skerlavaj, B. & Romeo, D. (1989) *Infect. Immun.* 57, 3142–3146.

Granger, D. N. & Korthuis, R. J. (1995) *Annu. Rev. Physiol.* 57, 311–332.

Hopp, T. P. (1985) in *Synthetic Peptides in Biology and Medicine*, Alitalo, K., Partanen, P. & Vaheri, A. (Elsevier Science Publishers), pp. 3–12.

Joseph, G., Gorzalczany, Y., Koshikin, V. & Pick, E. (1994) *J. Biol. Chem.* 269, 29024–29031.

Kilpatrick, L. E., Jakabovics. E., McCawley, L. J., Kane, L. H. & Korchak, H. M. (1995) *J. Immunol.* 154, 3429–3436.

Klebanoff, S. J. (1992) in *Inflammation: Basic Pnrnciples and Clinical Correlates*, eds. Gallin, J. I., Goldstein, I. M. & Snyderman, R. (Raven, N.Y.), pp. 541–588.

Lee, J.-Y., Boman, A., Chuanxin, S., Andersson, M., J ömvall, H., Mutt, V. & Boman, H. G. (1989) *Proc. Natl. Acad. Sci. USA* 86, 9159–9162.

Lehrer, R. I., Lichtenstein, A. K. & Ganz, T. (1993) *Annu. Rev. Immunol.* 11, 105–128.

Leto, T. L., Garrett, M. C., Fujii, H. & Nunoi, H. (1991) *J. Biol. Chem.* 266, 19812–19818.

Leto, T. L., Adams, A. G. & de Mendez, I. (1994) *Proc. Natl. Acad. Sci. USA* 91, 10650–10654.

Lim, W. A., Richards, F. M. & Fox, R. O. (1994) *Nature*, 372, 375–379.

Litteri, L. & Romeo. D. (1993) *Infect. Immun.* 61, 966–969.

MacKenzie, F. M. & Gould, I. M. (1993) *J. Antimicrobial Chemotherapy* 32, 519–537.

Malech, H. L. & Gallin, J. I. (1987) *New England J. Med.* 317, 687–694.

Maloy, W. L. & Prasad Kari, U. (1995) *Biopolymers (Peptide Science)* 37, 105–122.

Mann, D. A. & Frankel, A. D. (1991) *EMBO J.* 10, 1733–1739.

Martin, E., Ganz, T. & Lehrer, R. I. (1995) *J. Leukoc. Bio.* 58, 128–136.

Martinez-Cayuela, M. (1995) *Biochimie* 77, 147–161.

McPhail, L. C. (1994) *J. Exp. Med.* 180, 2011–2015.

McPhail, L. C., Qualliotine-Mann, D., Agwu, D. E. & McCall, C. E. (1993) *Eur. J. Haematol.* 51, 294–300.

Moore, K. S., Bevins, C. L., Tomassini, N., Huttner, K. M., Sadler, K., Moreira, J. E., Reynolds, J. & Zasloff. M. (1992) *J. Histochem. Cytochem.* 40, 367–378.

National Committee for Clinical Laboratory Standards. Methods for Dilution Antimicrobial Susceptibility Tests for Bacteria that Grow Aerobically, 2nd Ed.; Approved Standard NCCLS Document M7-A2, Vol 10. No. 8.

Rotrosen, D. (1992) in *Inflammation: Basic Principles and Clinical Correlates*, eds. Gallin, J. I., Goldstein, I. M. & Snyderman, R. (Raven, N.Y.), pp. 589–601.

Rotrosen, D., Yeung, C. L., Leto, T. L., Malech. H. L. & Kwong, C. H. (1992) *Science* 256, 1459–1462.

Salak, J. L., McGlone, J. J. & Lyte. M. (1993) *Vet. Immunol. Immunopathol.* 39, 327–337.

Schreck, R., Rieber, P. & Baeuerle, P. A. (1991) *EMBO J.*, 10, 2247–2258.

Selsted, M. E. & Ouellette, A. J. (1995) *Trends Cell Biol.* 5, 114–119.

Shasby, D. M., Vanbenthuysen, K. M., Tate, R. M., Shasby, S. S., McMurtry, I. & Repine, J. E. (1982) *Am. Rev. Resp. Dis.* 125, 443–447.

Shi, J., Goodband, R. D., Chengappa, M. M., Neissen, J. L., Tokach, M. D., McVey, D. S. & Blecha, F. (1994a) *J. Leukco. Biol.* 56, 88–94.

Shi, J., Ross, C. R., Chengappa, M. M. & Blecha, F. (1994b) *J. Leukco. Biol.* 56, 807–811.

Shi, J. & Blecha, F. (1995) *Conf. Res. Workers Anim. Dis.*, p. 48.

Shi, J., Ross, C. R., Chengappa, M. M., Sylte, M. J., McVey, D. S. & Blecha, F. (1996) *Antimicrob. Agents Chemother.*, 40, 115–121.

Steiner, H., Hultmark, D., Engstrom, A. Bennich, H. & Boman, H. G. (1981) *Nature* 292, 246248.

Sumimoto, H., Kage, Y., Nunoi, H., Sasaki, H., Nose, T., Fukumaki, Y., Ohno, M., Minakami. S. & Takeshige, K. (1994) *Proc. Natl. Acad. Sci. USA* 91, 5345–5349

Tafft, R. E. & Sitkovsky, M. V. (1992) *J. Pharmaceutical Sci.* 81, 3744.

Vallette, F. M., Juin, P. Pelleschi. M. & Henry, J.-P. (1994) *J. Biol. Chem.* 269, 13367–13374.

Zasloff, M. (1987) *Proc. Natl. Acad. Sci. USA* 84, 5449–5543.

Zasloff, M. (1992) *Current Opin. Immunol.* 4, 3–7.

---

What is claimed is:

1. A method of inhibiting leukocyte $O_2^-$ production comprising the step of contacting a leukocyte with a peptide selected from the group consisting of SEQ ID NOS: 1 and 2 for a time and under conditions effective to inhibit leukocyte $O_2^-$ production, wherein the inhibition of $O_2^-$ production occurs as a consequence of binding between the peptide and p47$^{phox}$, wherein said p47$^{phox}$ is a 47 kD cytosolic protein of the phagocyte NADPH oxidase complex.

2. The method of claim 1, wherein the peptide consists of SEQ ID NO: 1.

3. The method of claim 1, wherein the peptide is synthesized.

4. The method of claim 1, wherein the peptide inhibits the activity of NADPH oxidase.

5. The method of claim 1, wherein the leukocyie is a mammalian leukocyte.

6. The method of claim 5, wherein the leukocyte is a porcine leukocyte.

7. The method of claim 1, wherein the leukocyte is a neutrophil.

8. The method of claim 1, wherein said peptide binds to the SH3 domaim of p47$^{phox}$, and wherein said SH3 domaim refers to Src homology 3 domains in intact proteins in cytosolic components.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 39 amino acids
      (B) TYPE: amino acid
      (D) TOPOLOGY: linear (ii) MOLECULE TYPE: peptide (xi) SEQUENCE DESCRIPTION: SEQ ID NO:1:

```
Arg Arg Arg Pro Arg Pro Pro Tyr Leu Pro Arg Pro Arg Pro Pro Pro
1               5                  10                  15

Phe Phe Pro Pro Arg Leu Pro Pro Arg Ile Pro Pro Gly Phe Pro Pro
            20                  25                  30

Arg Phe Pro Pro Arg Phe Pro
        35
```

(2) INFORMATION FOR SEQ ID NO:2:

(i) SEQUENCE CHARACTERISTICS:
      (A) LENGTH: 26 amino acids
      (B) TYPE: amino acid
      (D) TOPOLOGY: linear (ii) MOLECULE TYPE: peptide (xi) SEQUENCE DESCRIPTION: SEQ ID NO:2:

```
Arg Arg Arg Pro Arg Pro Pro Tyr Leu Pro Arg Pro Arg Pro Pro Pro
1               5                  10                  15

Phe Phe Pro Pro Arg Leu Pro Pro Arg Ile
            20                  25
```

(2) INFORMATION FOR SEQ ID NO:3:

(i) SEQUENCE CHARACTERISTICS:
      (A) LENGTH: 23 amino acids
      (B) TYPE: amino acid
      (D) TOPOLOGY: linear (ii) MOLECULE TYPE: peptide (xi) SEQUENCE DESCRIPTION: SEQ ID NO:3:

```
Pro Arg Pro Pro Tyr Leu Pro Arg Pro Arg Pro Pro Pro Phe Phe Pro
1               5                  10                  15

Pro Arg Leu Pro Pro Arg Ile
        20
```

(2) INFORMATION FOR SEQ ID NO:4:

(i) SEQUENCE CHARACTERISTICS:

(A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:4:

Arg Arg Arg Pro Arg Pro Pro Tyr Leu Pro Arg Pro Arg Pro Pro
1               5                  10                  15

Phe Phe Pro (2) INFORMATION FOR SEQ ID NO:5:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:5:

Arg Pro Arg Pro Pro Pro Phe Phe Pro Pro Arg Leu Pro Pro Arg Ile
1               5                  10                  15

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:6:

Arg Ile Pro Pro Gly Phe Pro Pro Arg Phe Pro Pro Arg Phe Pro
1               5                  10                  15

(2) INFORMATION FOR SEQ ID NO:7:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:7:

Arg Arg Arg Pro Arg Pro Pro Tyr Leu Pro Arg Pro Arg Pro
1               5                  10

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:8:

Arg Pro Pro Pro Phe Phe Pro
1               5

(2) INFORMATION FOR SEQ ID NO:9:

(i) SEQUENCE CHARACTERISTICS:
        (A) LENGTH: 8 amino acids
        (B) TYPE: amino acid -continued (D) TOPOLOGY: linear (ii) MOLECULE TYPE: peptide (xi) SEQUENCE DESCRIPTION: SEQ ID NO:9:

Pro Pro Arg Leu Pro Pro Arg Ile
1               5